US012564374B2

(12) United States Patent
Amans

(10) Patent No.: US 12,564,374 B2
(45) Date of Patent: Mar. 3, 2026

(54) SPINAL CEREBRAL ARTERY RUPTURE DETECTOR

(71) Applicant: The Regents of the University of California, Oakland, CA (US)

(72) Inventor: Matthew Amans, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 149 days.

(21) Appl. No.: 18/279,890

(22) PCT Filed: Mar. 3, 2022

(86) PCT No.: PCT/US2022/018658
§ 371 (c)(1),
(2) Date: Sep. 1, 2023

(87) PCT Pub. No.: WO2022/187454
PCT Pub. Date: Sep. 9, 2022

(65) Prior Publication Data
US 2024/0148355 A1 May 9, 2024

Related U.S. Application Data

(60) Provisional application No. 63/155,997, filed on Mar. 3, 2021.

(51) Int. Cl.
A61B 8/08 (2006.01)
A61B 8/00 (2006.01)

(52) U.S. Cl.
CPC .......... A61B 8/0891 (2013.01); A61B 8/4236 (2013.01); A61B 8/4477 (2013.01); A61B 8/461 (2013.01); A61B 8/488 (2013.01)

(58) Field of Classification Search
None
See application file for complete search history.

(56) References Cited

U.S. PATENT DOCUMENTS

| | | |
|---|---|---|
| 2003/0199784 A1 | 10/2003 | Lenhardt |
| 2005/0015009 A1 | 1/2005 | Mourad et al. |
| 2011/0201961 A1 | 8/2011 | Hu et al. |
| 2017/0281020 A1* | 10/2017 | Mulligan ........... A61B 5/02042 |
| 2018/0279995 A1* | 10/2018 | Doyle .................. A61B 8/5223 |
| 2021/0113194 A1* | 4/2021 | Padwal ................. G06T 7/0012 |

OTHER PUBLICATIONS

Hocking, K. M. et al., "Peripheral Venous Waveform Analysis for Detecting Hemorrhage and Iatrogenic Volume Overload in a Porcine Model." Shock 46.4 (2016): 447-452.

(Continued)

*Primary Examiner* — Jonathan Cwern

(74) *Attorney, Agent, or Firm* — Carter, DeLuca & Farrell LLP; Vadim Vapnyar

(57) ABSTRACT

A system for detecting a blood vessel rupture is disclosed. The system includes a sensor assembly including a plurality of sensors, each of which is configured to detect a pressure wave through CSF and to generate a pressure signal in response thereto. The system also includes a processing device coupled to the sensor assembly. The processing device configured to analyze the pressure signal to determine a blood vessel rupture.

18 Claims, 4 Drawing Sheets

(56)                    References Cited

OTHER PUBLICATIONS

Kawoos, U. et al., "Advances in Intracranial Pressure Monitoring and Its Significance in Managing Traumatic Brain Injury." International journal of molecular sciences 16.12 (2015):28979-28997.
International Search Report and Written Opinion of the International Searching Authority issued in corresponding application PCT/US2022/018658 mailed May 18, 2022 (7 pages).

* cited by examiner

SPINAL CEREBRAL ARTERY RUPTURE DETECTOR

CROSS REFERENCE TO RELATED APPLICATIONS

The present application is a U.S. National Stage Application filed under 35 U.S.C. § 371(a) of International Patent Application No. PCT/US2022/018658, filed on Mar. 3, 2022, which claims the benefit of and priority to U.S. Provisional Application No. 63/155,997, filed on Mar. 3, 2021. The entire disclosures of the foregoing applications are incorporated by reference herein.

BACKGROUND

An estimated six million people have brain aneurysms with an annual rupture rate of about 8-10 per 100,000. An aneurysm may rupture during an endovascular surgical procedure treating the aneurysm, or during any other endovascular procedure. Similarly, endovascular rupture of cerebral arteries can occur during treatment of acute ischemic stroke, arteriovenous malformations, arterial stenosis, and other vascular diseases. Such rupture events, while rare, can be life threatening. The sooner the surgeon/operator is aware of the rupture, the quicker they can act to treat the rupture and increase the odds of survival.

Endovascular therapy continues to become the mainstay of treatment of cerebrovascular diseases, yet training continues to be insufficient. In many institutions, simply graduating from a neurosurgical residency without dedicated training in endovascular surgery (which itself is typically a 2-year fellowship) is considered to be adequate for certification. Thus, with increasing reliance on endovascular techniques, and decreasing requirements for dedicated training in the field, intra-procedural ruptures are becoming more and more common events.

In addition, endovascular treatment of acute ischemic stroke is now considered to be a standard of care. One of the rare events that can occur is a tear (i.e., due to perforation, dissection, or rupture) in the intracranial vasculature. This can also be a life-threatening event and may not be immediately recognizable due to the chaotic, time sensitive, emergent nature of these procedures, which require moving as quickly as possible to try and revascularize the patient. Thus, there is a need for a system and method to detect rupture of aneurysms and other cerebral vascular deformities, or perforation/rupture of any normal cerebral artery during endovascular surgical procedures.

SUMMARY

The present disclosure provides a system and method for detecting cerebral vascular ruptures during endovascular surgical procedures, including treatment of aneurysms, acute ischemic strokes, and the like. A sensor assembly including a plurality of noninvasive probes or sensors is disposed along the patient's spine and is configured to measure the depth of the dura relative to the skin. The device is configured to detect an intraprocedural rupture of a cerebral vascular deformity (such as aneurysm, arteriovenous malformation, fistula, stenosis, or other vascular disease) during endovascular treatment.

More specifically, a rupture results in a pressure wave being instilled into the cerebrospinal fluid ("CSF"). This can be sometimes identified using an indwelling external ventricular drain, when present, or neurostimulating monitors that obfuscate the view of the aneurysm and its treatment. Most surgeons do not use neurostimulating monitors for this reason, and many patients have aneurysms treated without needing an external ventricular drain. In addition, an external ventricular drain is not used in an acute stroke intervention or elective embolization of a vascular malformation.

The device according to the present disclosure is configured to detect this pressure wave without requiring a catheter to be placed within the patient's brain or spine, or large numbers of metallic devices placed over the head that obscure the view of the endovascular surgery. Thus, the device according to the present disclosure allows the surgeon to more quickly respond to this life-threatening event, and potentially save the patient's life without the limitations of conventional monitoring devices and methods.

According to one embodiment of the present disclosure, a system for detecting a blood vessel rupture is disclosed. The system includes a sensor assembly including a plurality of sensors, each of which is configured to detect a pressure wave through CSF and to generate a pressure signal in response thereto. The system also includes a processing device coupled to the sensor assembly, the processing device is configured to analyze the pressure signal to determine a blood vessel rupture.

Implementations of the above embodiment may include one or more of the following features. According to one aspect of the above embodiment, the sensor assembly includes a substrate defining a primary longitudinal axis and the sensors are disposed in an array along the primary longitudinal axis. The sensors may be disposed in an undulating pattern. The sensors may also be arranged in at least one group defining a secondary axis that is transverse to the primary longitudinal axis. Each of the sensors may be one of an ultrasound Doppler transducer, traditional ultrasound transducer, an optical Doppler transducer, or a light-based sensor. The processing device may also include a storage device storing a database of signal waveforms corresponding to a blood vessel ruptures. The processing device is further configured to make a determination that the blood vessel rupture has occurred based on a comparison of the pressure signal to the signal waveforms, or a waveform determined by the depth of the dura. The system may also include a display and the processing device may be further configured output an alarm in response to the determination of the blood vessel rupture. The processing device may also be configured to store the pressure signals as signal waveforms in the database.

According to another embodiment of the present disclosure, a method for detecting a blood vessel rupture is disclosed. The method includes placing a sensor assembly on a back of a patient, the sensor assembly including a plurality of sensors each of which is configured to detect a pressure wave through CSF and to generate a pressure signal in response thereto. The method also includes analyzing the pressure signal at a processing device coupled to the sensor assembly to determine a blood vessel rupture.

Implementations may include one or more of the following features. According to one aspect of the above embodiment, the method may also include: verifying proper placement of the sensory assembly at the processing device. Verification of proper placement may include analyzing a signal of each sensor of the plurality of sensors to determine the signal is adequate. The sensor assembly may include a substrate defining a primary longitudinal axis and the sensors are disposed in an array along the primary longitudinal axis. The sensors may be disposed in an undulating pattern. The sensors may also be arranged in at least one group defining a secondary axis that is transverse to the primary longitudinal axis. Each of the sensors may be one of an ultrasound transducer or an optical transducer with or without Doppler technology. The method may also include storing a plurality of prerecorded signal waveforms corresponding to blood vessel ruptures in a databased in a storage device of the processing device. The method may further include determining the blood vessel rupture has occurred based on a comparison of the pressure signal to the signal waveforms. The method may also include outputting an alarm on a display in response to the determination of the blood vessel rupture. The method may further include categorizing the pressure signals; and storing the categorized pressure signals as the signal waveforms in the database.

BRIEF DESCRIPTION OF THE DRAWINGS

Embodiments of the present disclosure are described herein with reference to the accompanying drawings, wherein.

DETAILED DESCRIPTION

Figure 1:
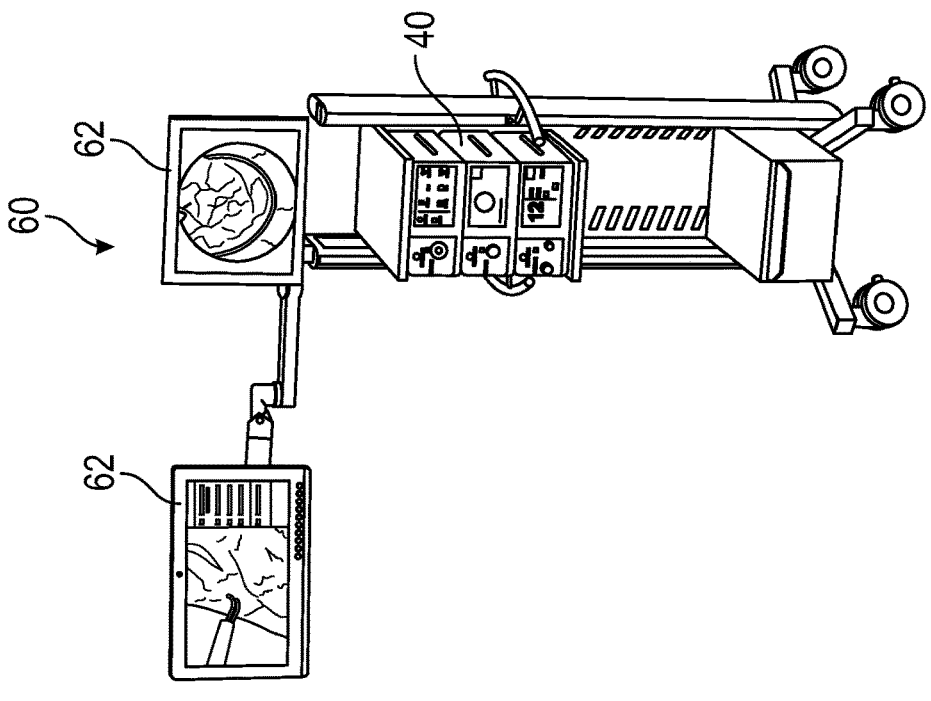
FIG. 1 is a diagram of a system for detecting a blood vessel rupture according to an embodiment of the present disclosure.
Figure 1:
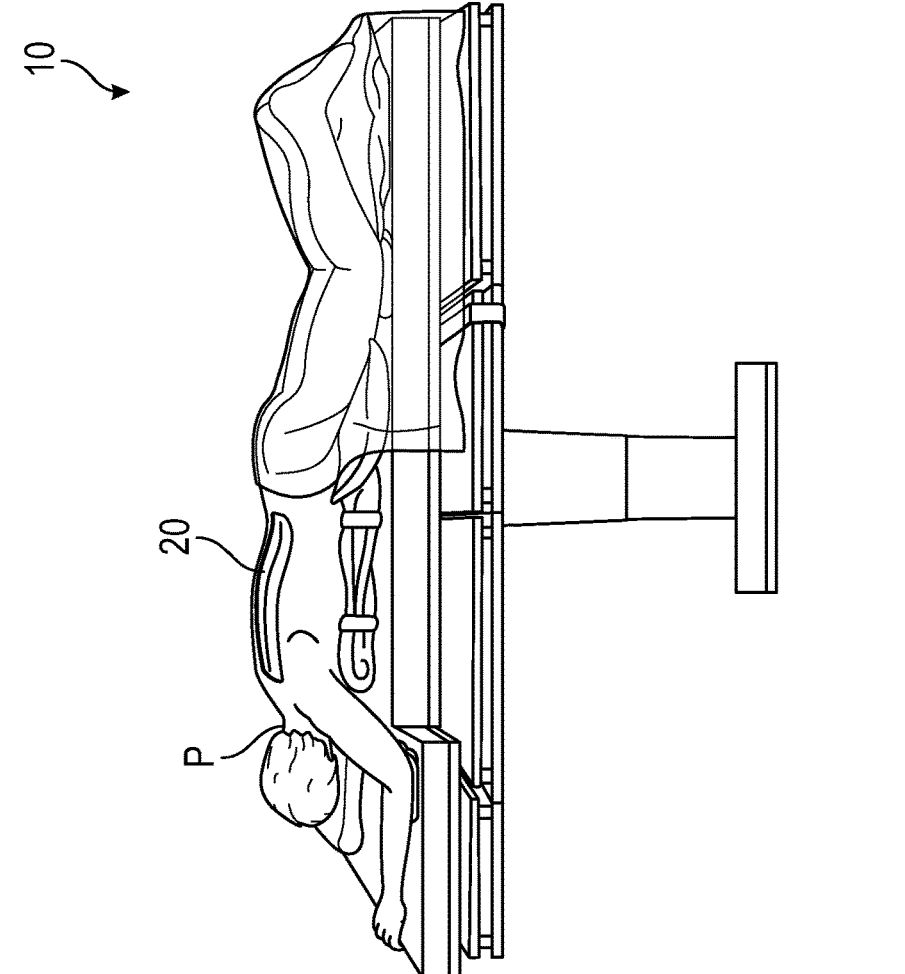

Embodiments of the present disclosure are described in detail with reference to the drawings, in which like reference numerals designate identical or corresponding elements in each of the several views. As used herein the term "proximal" refers to the portion of a device that is closer to the user, while the term "distal" refers to the portion that is farther from the user. The term "about" denotes a range of ±5% from the stated value.

FIG. 1 shows a surgical system 10 for detecting blood vessel ruptures of a cerebral vascular deformity during endovascular surgical procedures. As used herein, a vascular deformity denotes any other vascular disease, such as an aneurysm, an arteriovenous malformation, a fistula, a stenosis, and the like. The system 10 includes a sensor assembly 20 disposed on a patient "P". The sensor assembly 20 is configured to measure pressure waves travelling through the spinal cerebral fluid, which is adjacent spinal cerebral artery.

The sensor assembly 20 is coupled to a processing device 40 configured to process pressure sensor signals from the sensor assembly 20 to determine occurrence of a blood vessel rupture based on pressure waves traveling through the CSF. The processing device 40 is coupled to operating room equipment 60 configured to display the current state of the spinal cerebral artery and/or alarms based on the output of the sensor assembly 20.

Figure 2:
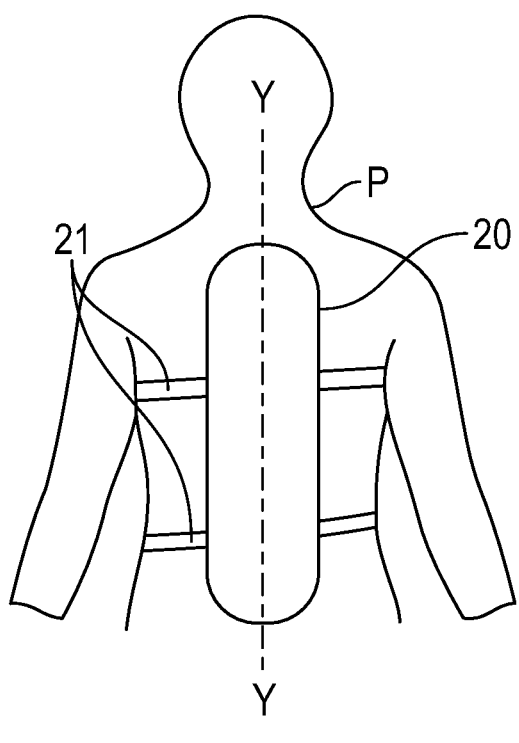
FIG. 2 is a diagram of the sensor assembly of the system of FIG. 1 disposed on a back of a patient.
Figure 3:
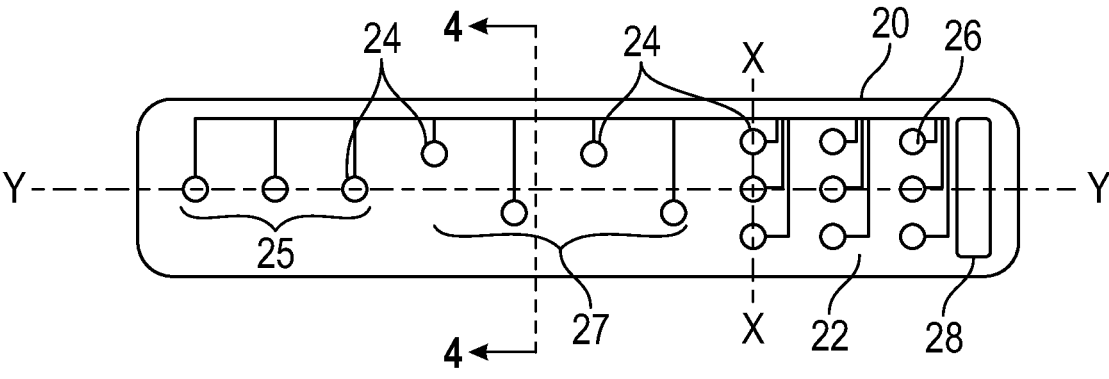
FIG. 3 is a schematic plan view of the sensor assembly of FIG. 2 according to an embodiment of the present disclosure.
Figure 4:
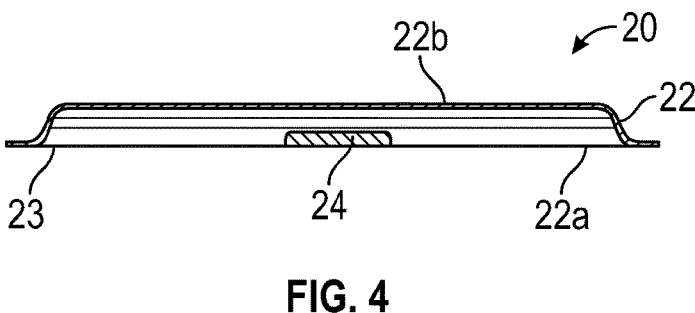
FIG. 4 is a cross-sectional view along the line "4-4" of the sensor assembly of FIG. 2 according to an embodiment of the present disclosure.

With reference to FIGS. 2-4, the sensor assembly 20 is disposed on a back of the patient "P." The sensor assembly 20 includes a substrate 22 having an inner surface 22a and an outer surface 22b. The inner surface 22a is in contact with the back of the patient "P". The substrate 22 may have a multi-layered structure with a plurality of sensors 24 disposed on the inner surface 22a, such that the sensors 24 are in contact with the patient "P", on the outer surface 22b, or in between the layers of the substrate 22. In embodiments, the inner surface 22a may include an adhesive backing 23 (FIG. 4) configured to secure the sensor assembly 20 to the patient "P". In further embodiments, the sensor assembly 20 may have one or more bands 21 (FIG. 2) configured to secure the sensor assembly 20 to the torso of the patient "P". The substrate 22 may be formed from any suitable flexible material configured to conform the back of the patient "P", such as multi-layered polymeric films.

With reference to FIG. 3, the sensors 24 are disposed along a longitudinal axis "Y-Y" of the sensor assembly 20, such that the sensors 24 are aligned with a spine of the patient "P" along the spinal canal. In particular, the sensor assembly 20 is disposed along the thoracic or lumbar region of the spine. This allows the sensors 24 to measure pressure waves traveling through the CSF, which occur due to rupture of the aneurysm(s) and other blood vessels.

The sensors 24 may be any sensors configured to measure pressure fluctuations in the CSF, such as ultrasound Doppler transducers or optical Doppler transducers. The sensors 24 are disposed in a longitudinal array 25 along the longitudinal axis "Y-Y." The sensors 24 may be disposed in an undulating pattern 27 along the longitudinal axis or in a straight line. In further embodiments, a plurality of the sensors 24 may be disposed in one or more groups 26 disposed about one or more of the vertebrae substantially along an axis "X-X" (i.e., group axis) that is transverse to the longitudinal axis "Y-Y" (i.e., array axis). The sensors 24 may be grouped according to one or more of the above-described groups and/or patterns. The sensors 24 and/or groups 26 of the sensors 24 may be spaced along the longitudinal array 25 by about a vertebral body length.

Each of the sensors 24 are coupled to a communication interface 28, which may be a local wired bus or a wireless interface. The communication interface 28 also includes an external wired or wireless interface for communicating with the processing device 40. The communication interface 28 may include an antenna and any other suitable transceiver circuitry configured to communicate with the sensors 24 and/or the processing device 40 using wireless communication protocols. Wireless communication may be achieved via one or more wireless configurations, e.g., radio frequency, optical, Wi-Fi, ANT+, BLUETOOTH®, (an open wireless protocol for exchanging data over short distances, using short length radio waves, from fixed and mobile devices, creating personal area networks (PANs), ZIGBEE® (a specification for a suite of high level communication protocols using small, low-power digital radios based on the IEEE 802.15.4-2003 standard for wireless personal area networks (WPANs)), and the like.

Figure 5:
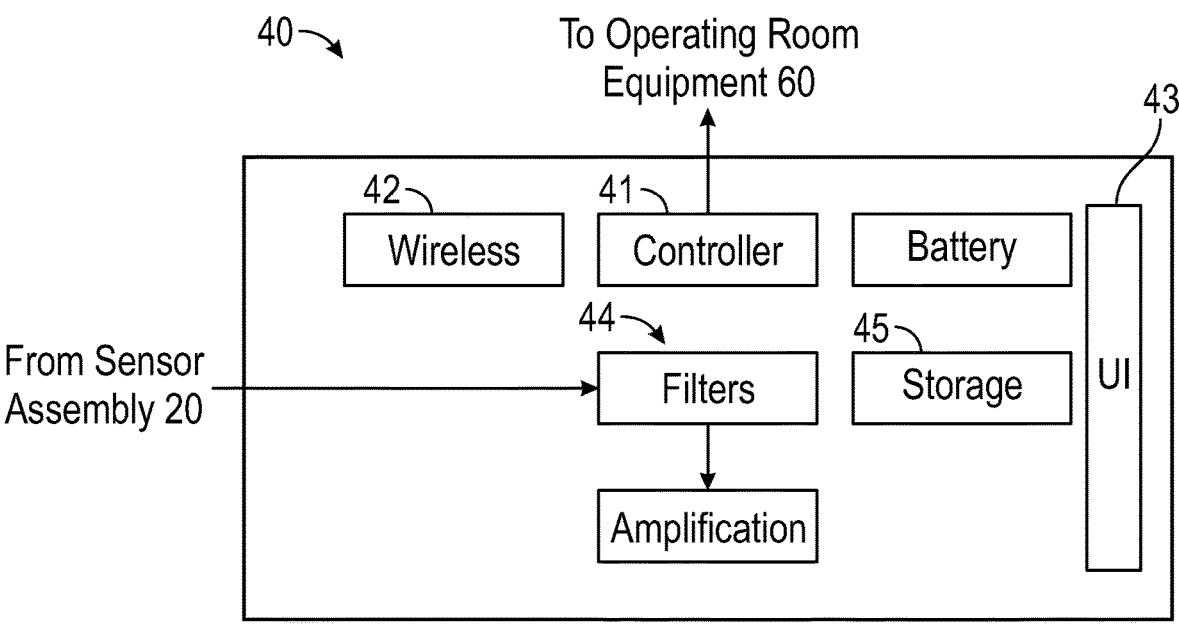
FIG. 5 is a block diagram of a processing device of the system of FIG. 1 according to an embodiment of the present disclosure.

With reference to FIG. 5, the processing device 40 includes a controller 41, which may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted by any logic processor (e.g., control circuit) adapted to execute algorithms, calculations, and/or set of instructions described herein.

The controller 41 may also include a memory, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The controller 41 and the memory device may be any standard processor and memory component known in the art.

The processing device 40 further includes a wireless interface 42, which may include an antenna and any other suitable transceiver circuitry configured to communicate with external devices (i.e., the sensor assembly 20 and the operating room equipment 60) using wireless communication protocols. The processing device 40 may also include a user input device 43, having a display, i.e., a touchscreen and/or one or more buttons, which allows for the user to control operation of the processing device 40.

The processing device 40 further includes a signal processing circuit 44, which may include discrete components or may be configured as a single circuit. The signal processing circuits 44 may be analog or digital, which may be embodied in the controller 41. The sensor signals may be digitized by using any suitable method, such as Fourier transform algorithms. The processing device 40 may include any suitable electronic components, such as analog-to-digital (A/D) converters to digitize the sensor signal.

One of the signal processing circuits 44 may be a filtering circuit, which may include one or more of the following filters: high pass, low pass, band pass, notch filters and/or digital equivalents thereof. The filtered sensor signal may also be amplified through an amplifier. In embodiments, the user input device 43 may be provided by the operating room equipment 60, obviating the need for standalone components.

The processing device 40 also includes a storage device 45 for storing recorded sensor signals. The storage device 45 may include a database of prerecorded signals corresponding to various events generating specific signal waveforms, including aneurysm ruptures which generate a traveling pressure wave in the CSF. Stored signals may be categorized based on the type of pressure fluctuations event. More specifically, a blood vessel rupture generates a specific waveform "signature," which includes a specific pattern, such as an increase in CSF pressure, or a transient increase in the CSF pressure that causes a temporary deflection in the dura mater (e.g., a plateau) having a duration from about 10 ms to about 500 ms followed by a drop off.

In further embodiments, the processing device 40 may continuously update the database during its operation. The processing device 40 is configured to identify and categorize the recorded signals into the categories defined in the database. In embodiments, the processing device 40 may define new categories if the recorded signal does not fall within one of the prescribed categories. The processing device 40 then stores the recorded signals as signal waveforms in the database. In further embodiments, the database may be a shared (e.g., cloud-based) database accessible by a plurality of processing devices 40 such that additional data from a plurality of sources is utilized to build and update the database of signal waveforms.

Sortation and identification of the signal waveforms may be done automatically by the processing device 40 using machine learning. It is envisioned that there may be an ongoing training of the identification process to automatically identify the pressure fluctuation events corresponding to specific signals using artificial intelligence.

The terms "artificial intelligence," "data models," or "machine learning" may include, but are not limited to, neural networks, convolutional neural networks (CNN), recurrent neural networks (RNN), generative adversarial networks (GAN), Bayesian Regression, Naive Bayes, nearest neighbors, least squares, means, and support vector regression, among other data science and artificial science techniques.

A neural network may be used to train the processing device 40. In various embodiments, the neural network may include a temporal convolutional network, with one or more fully connected layers, or a feed forward network. In various embodiments, training of the neural network may happen on a separate system, e.g., graphic processor unit ("GPU") workstations, high performing computer clusters, etc., and the trained algorithm would then be deployed on the processing device 40. In further embodiments, training of the neural networks may happen locally, e.g., on the processing device 40 and/or the computing device 40. After training, the processing device 40 may include a software application that is executable by the controller 41 to identify and sort various recorded pressure waveforms into corresponding storage banks.

During operation, the processing device 40 continuously receives signals from the sensor assembly 20 and its plurality of sensors 24. The processing device 40 compares pressure signal waveforms from each of the sensors 24 to the waveforms in the database to identify ruptures. The processing device 40 may use pressure signal waveforms from a plurality of sensors 24 to confirm that a rupture has occurred, to avoid false alarms due to false positives from only a single sensor 24. Once a rupture is confirmed, the processing device 40 outputs an alarm via the operating room equipment 60, which may include one or more monitors 62, and/or through a surgical console of a surgical robotic system.

Figure 6:
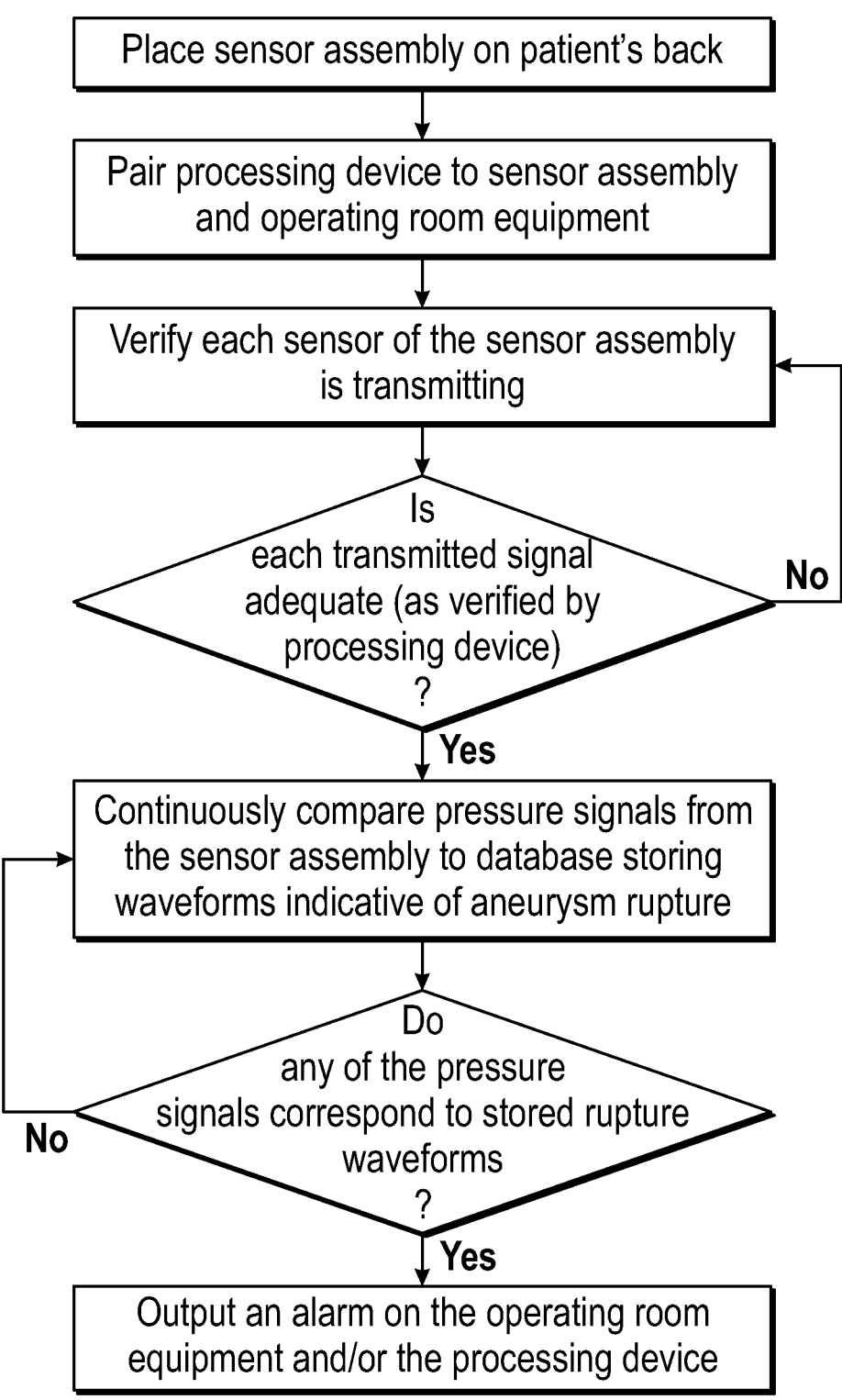
FIG. 6 is a flow chart of a method for detecting a blood vessel rupture according to an embodiment of the present disclosure.

With reference to FIG. 6, a flow chart of a method for detecting a blood vessel rupture is shown. During preparation for the surgical procedure, the sensory assembly 20 is placed on the back of the patient "P" as shown in FIG. 2. The sensor assembly 20 is also connected and/or paired to the processing device 40, which itself is also connected and/or paired to the operating room equipment 60. Once connection is confirmed, the processing device 40 confirms that the sensor assembly 20 is properly positioned on the patient "P." The processing device 40 verifies that each of the sensors 24 is transmitting a signal corresponding to normal pressure readings within the CSF surrounding the spine. In embodiments, the processing device 40 may confirm that at least one of the sensors 24 of the group 26 is transmitting an adequate signal. Based on the confirmation criteria, the processing device 40 outputs a prompt through the user input device 43 and/or the monitors 62 to enable the surgical staff to adjust the sensor assembly 20 such that the sensors 24 previously transmitting inadequate signals are adjusted to provide an adequate signal. This process is repeated until a sufficient number (i.e., all) of the sensors 24 are transmitting an adequate signal.

Once the sensor assembly 20 is properly positioned on the patient "P" the surgical procedure is commenced, during which the processing device 40 continuously receives and processes sensor signals from the sensors 24 of the sensor assembly 20. The processing device 40 compares the signal waveforms to the stored waveforms indicative of rupture events. If a rupture event is detected, based on a substantial (e.g., 95% or above) match of the signal waveform to the waveforms stored in the database, the processing device 40 outputs an audio and/or visual alarm through the user input device 43 and/or the monitors 62. In addition, the processing device 40 may also record all or any portion of the sensor signals for subsequent processing and updating of the database to provide a more accurate template for rupture detection.

It will be appreciated that of the above-disclosed and other features and functions, or alternatives thereof, may be desirably combined into many other different systems or applications. Various presently unforeseen or unanticipated alternatives, modifications, variations or improvements may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A system for detecting a blood vessel rupture, the system comprising:
 a sensor assembly configured to measure a pressure wave traveling through cerebrospinal fluid (CSF) caused by a blood vessel rupture, the sensor assembly including:
   a substrate configured to be placed on a patient such that the substrate is positioned along a spinal canal;
   a plurality of sensors disposed on the substrate, each sensor of the plurality of sensors configured to detect the pressure wave through the CSF and to generate a pressure signal in response thereto; and
 a processing device coupled to the sensor assembly, the processing device configured to determine a blood vessel rupture has occurred based on a comparison of the pressure signal to a plurality of signal waveforms corresponding to blood vessel ruptures.

2. The system according to claim 1, wherein the substrate defines a primary longitudinal axis and the plurality of sensors are disposed in an array along the primary longitudinal axis.

3. The system according to claim 2, wherein the plurality of sensors are disposed in an undulating pattern.

4. The system according to claim 2, wherein the plurality of sensors are arranged in at least one group defining a secondary axis that is transverse to the primary longitudinal axis.

5. The system according to claim 1, wherein each sensor of the plurality of sensors is one of an ultrasound Doppler transducer or an optical Doppler transducer.

6. The system according to claim 1, wherein the processing device includes a storage device storing a database of signal waveforms corresponding to ruptures.

7. The system according to claim 6, wherein the processing device is configured to store the pressure signals as the plurality of signal waveforms in the database.

8. The system according to claim 1, further comprising a display and the processing device is configured output an alarm in response to the determination of the blood vessel rupture.

9. A method for detecting a blood vessel rupture, the method comprising:
 placing a substrate of a sensor assembly on a patient such that the substrate is positioned along a spinal canal of a patient, the sensor assembly including a plurality of sensors disposed on the substrate;
 measuring, using the sensor assembly, a pressure wave traveling through cerebrospinal fluid (CSF) caused by a blood vessel rupture;
 generating a pressure signal in response to the measured pressure wave; and
 determining at a processing device coupled to the sensor assembly a blood vessel rupture has occurred based on a comparison of the pressure signal to a plurality of signal waveforms corresponding to blood vessel ruptures.

10. The method according to claim 9, further comprising:
 verifying proper placement of the sensory assembly at the processing device.

11. The method according to claim 10, wherein verification of proper placement includes analyzing the pressure signal of each sensor of the plurality of sensors to determine the pressure signal is adequate.

12. The method according to claim 9, wherein the substrate defines a primary longitudinal axis and the sensors are disposed in an array along the primary longitudinal axis.

13. The method according to claim 12, wherein the plurality of sensors are disposed in an undulating pattern.

14. The method according to claim 12, wherein the plurality of sensors are arranged in at least one group defining a secondary axis that is transverse to the primary longitudinal axis.

15. The method according to claim 9, wherein each sensor of the plurality of sensors is one of an ultrasound Doppler transducer or an optical Doppler transducer.

16. The method according to claim 9, further comprising storing a plurality of prerecorded signal waveforms corresponding to blood vessel ruptures in a database in a storage device of the processing device.

17. The method according to claim 16, outputting an alarm on a display in response to the determination of the blood vessel rupture.

18. The method according to claim 16, further comprising:
 categorizing the pressure signals; and
 storing the categorized pressure signals as the plurality of signal waveforms in the database.

\* \* \* \* \*